(12) United States Patent
Mlodinow et al.

(10) Patent No.: US 11,389,281 B1
(45) Date of Patent: Jul. 19, 2022

(54) SURGICAL MESH (71) Applicant: SURGICAL INNOVATION ASSOCIATES, INC., Chicago, IL (US)

(72) Inventors: Alexei Mlodinow, Chicago, IL (US); Jamie Li, Chicago, IL (US); Todd Cruikshank, Chicago, IL (US); Ketan Yerneni, Chicago, IL (US)

(73) Assignee: Surgical Innovation Associates, Inc., Chicago, IL (US)

( * ) Notice: Subject to any disclaimer, the term of this patent is extended or adjusted under 35 U.S.C. 154(b) by 401 days.

(21) Appl. No.: 16/661,357

(22) Filed: Oct. 23, 2019

Related U.S. Application Data (60) Provisional application No. 62/749,483, filed on Oct. 23, 2018.

(51) Int. Cl.
*A61F 2/00* (2006.01)
*D04B 21/10* (2006.01)

(52) U.S. Cl.
CPC ............ *A61F 2/0063* (2013.01); *D04B 21/10* (2013.01); *A61F 2002/0068* (2013.01); *A61F 2240/001* (2013.01); *D10B 2509/08* (2013.01)

(58) Field of Classification Search
CPC .... A61F 13/00017; A61F 2/00; A61F 2/0009; A61F 2/0022; A61F 2/0036; A61F 2/0045; A61F 2/0063; A61F 2/0077; A61F 2/02; A61F 2/105; A61F 2/12; A61F 2002/0068; A61F 2002/0086; A61F 2002/045; A61F 2002/30032; A61F 2002/30062; A61F 2002/30158; A61F 2002/30784; A61F 2002/30914; A61F 2002/3092; A61F 2002/4435; A61F 2013/00659; A61F 2210/0004; A61F 2210/0057;

(Continued)

(56) References Cited

U.S. PATENT DOCUMENTS 5,569,273 A * 10/1996 Titone .................... D04B 21/12
                                           606/151
5,611,986 A * 3/1997 Datta .................... A61L 17/12
                                           264/234

(Continued)

FOREIGN PATENT DOCUMENTS

EP          0647669 A2 * 12/1995 ............. A61L 31/06

OTHER PUBLICATIONS

Abhari et al., "Effect of annealing on the mechanical properties and the degradation of electrospun polydioxanone filaments," Journal of the Mechanical Behavior of Biomedical Materials, Elsevier, Mar. 2017, vol. 67, pp. 127-134.

(Continued)

*Primary Examiner* — Kaylee R Wilson
*Assistant Examiner* — Marc D. Honrath
(74) *Attorney, Agent, or Firm* — Leydig, Voit & Mayer, Ltd.

(57) ABSTRACT

A method for creating a surgical mesh includes heat treating a plurality of fibers; knitting the plurality of fibers into a mesh; and heat treating the mesh by applying heat at a temperature that falls within a range of 65 degrees Celsius to 110 degrees Celsius while subjecting the mesh to a tension that falls in a range of 4.0 Newtons per centimeter (N/cm) to 32.0 N/cm for a period of time that falls in a range of 1 hour to 9 hours.

20 Claims, 10 Drawing Sheets

(58) Field of Classification Search
CPC ...... A61F 2210/0076; A61F 2210/0075; A61F 2230/0026; A61F 2230/0063; A61F 2240/00; A61F 2240/001; A61F 2250/0012; A61F 2250/0017; A61F 2250/0018; A61F 2250/0023; A61F 2250/003; A61F 2250/0031; A61L 2/0023; A61L 2/0035; A61L 2/007; A61L 2202/181; A61L 2300/604; A61L 2400/18; A61L 2430/34; A61L 26/0085; A61L 26/009; A61L 27/3629; A61L 27/54; A61L 27/56; A61L 31/00; A61L 31/146; A61L 31/148; A61L 31/16; A61L 33/007; D10B 2401/12; D10B 2509/04; D10B 2509/08
See application file for complete search history.

(56) References Cited

U.S. PATENT DOCUMENTS

| | | | | |
|---|---|---|---|---|
| 6,261,677 | B1* | 7/2001 | Tsai | C08G 63/88 428/113 |
| 9,937,282 | B2* | 4/2018 | Gingras | A61F 2/0063 |
| 2012/0071566 | A1* | 3/2012 | Kelly | A61L 31/16 606/228 |
| 2016/0151137 | A1* | 6/2016 | Egnelöv | A61F 2/0063 606/151 |

OTHER PUBLICATIONS

Canady et al., "Craniofacial Growth in Rabbits After Rigid or Semi-rigid Fixation of the Frontonasial Suture," Plastic and Reconstructive Surgery, Lippincott Williams & Wilkins, U.S., Sep. 1996; vol. 98 (3), pp. 410-417.

Cascone et al., "Rigid Versus Semirigid Fixation for Condylar Fracture: Experience With the External Fixation System," Journal of Oral and Maxillofacial Surgery, Elsevier, Feb. 2008, vol. 66 (2), pp. 265-271.

Jones et al., "Rigid fixation: A review of concepts and treatment of fractures," Oral Surgery, Oral Medicine, Oral Pathology, Elsevier, Jan. 1988, vol. 65 (1), pp. 13-18.

Onen et al., "Comparison of rigid and semi-rigid instrumentation under acute load on vertebrae treated with posterior lumbar interbody fusion/transforaminal lumbar interbody fusion procedures: An experimental study," Proceedings of the Institution of Mechanical Engineers Part H, Journal of Engineering in Medicine, 2018, pp. 1-7.

Patel et al., "Titanium mesh (TiMesh) osteosynthesis: a fast and adaptable method of semi-rigid fixation," British Journal of Oral and Maxillofacial Surgery, Elsevier, Oct. 1991, vol. 29 (5), pp. 316-324.

Paulus, "Semirigid Bone Fixation: A New Concept in Orthognathic Surgery," Journal of Craniofacial Surgery, Dec. 1991, vol. 2 (3), pp. 146-151.

* cited by examiner

BREAKING STRENGTH OF A HEALING SKIN INCISION IN THE RAT

Simple plot of breaking strength of a
healing skin incision in rat as a function of healing time

FIG. 4A

TENSILE STRENGTH OF A HEALING SKIN INCISION IN THE RAT

Tensile strength of a healing skin incision
as a function of time

FIG. 4B

TABLE 1. The Breaking and Tensile Strength of Healing Skin Wounds of Rats

| Wound Age Days | No. Rats | Sacrifice Body Wt.* Gm. | Fresh Breaking Strength of DSI** Gm. | Fresh Thickness** mm. | Fresh Tensile Strength** Grams/sq. mm. | Formalin Fixed Breaking Strength of DSI** Grams |
|---|---|---|---|---|---|---|
| 7   | 10 | 295±12 | 210±18    | 1.35±.02 | 26±4   | 635±48 |
| 14  | 10 | 323±17 | 515±59    | 1.42±.03 | 64±7   | 1420±74 |
| 21  | 10 | 343±26 | 1350±92   | 1.38±.03 | 163±13 | 2740±100 |
| 28  | 10 | 368±23 | 2990±168  | 1.46±.04 | 343±22 | 4000±127 |
| 28  | 22 | 349±16 | 2730±114  | 1.47±.03 | 313±18 | 4880±160 |
| 42  | 22 | 371±15 | 5260±206  | 1.48±.03 | 626±27 | 7225±318 |
| 61  | 21 | 421±32 | 6395±252  | 1.45±.04 | 746±22 | 9244±358 |
| 90  | 21 | 477±27 | 7475±215  | 1.70±.05 | 600±28 | 11189±408 |
| 90  | 23 | 462±42 | 7850±235  | 1.45±.03 | 923±41 | 10199±308 |
| 184 | 21 | 512±32 | 7420±274  | 2.16±.05 | 646±33 | 10052±278 |
| 240 | 22 | 572±42 | 7790±165  | 2.22±.06 | 584±30 | 10620±312 |
| 365 | 22 | 576±62 | 7890±248  | 1.91±.05 | 690±28 | 9290±342 |

*Mean ± Standard Deviation.
** Mean ± Standard Error.
All differences in successive values of both breaking strength and tensile strength are statistically significant through day 42.

SURGICAL MESH

CROSS-REFERENCE TO RELATED APPLICATIONS

This application claims the priority benefit of U.S. Provisional Application No. 62/749,483, filed Oct. 23, 2018 and incorporated herein by reference in its entirety.

BACKGROUND

Surgical mesh is a sterile, biocompatible fabric that can be stitched into soft tissue to reinforce weakness or bridge gaps within the body. The three characteristics of surgical mesh—sterility, biocompatibility, and physical properties—all vary significantly among currently-available products.

DRAWINGS

Features of the present techniques may be best understood from the following detailed description taken in conjunction with the accompanying drawings of which.

DETAILED DESCRIPTION

The disclosure is generally directed to an absorbable surgical mesh with certain parameters of construction that yield an ideal combination of strength retention and timely disappearance from the body. In an embodiment, these characteristics are achieved through selection of certain parameters of construction using thermoplastic polymer.

Three characteristics of surgical mesh are sterility, biocompatibility, and physical properties.

Sterility: Multiple methods of sterilization are available, as are multiple levels of "sterility assurance." Generally, meshes must (according to regulatory standards) be sterilized to a "sterility assurance level" (SAL) of 10-6. This indicates (statistically) that less than one in one million articles will have a viable micro-organism. However, there are less stringent regulatory requirements for the sterilization of certain biologic meshes that are derived from human tissue, and these sometimes achieve an SAL of only 10-3. Sterilization can be achieved with heat (autoclave, etc), chemicals (EtO, H2O2, etc), or radiation (e-beam, gamma, etc). Each has conditions necessary to achieve reliable and reproducible results, and each has its risks with respect to the material of the mesh and the changes it might confer. As one example radiation may cross-link polymers, making them stronger, but more brittle, and less predictable in their hydrolysis. As another example, EtO sterilization requires a humid environment with H2O as a carrier molecule, yet some mesh products may degrade via hydrolysis, meaning they are susceptible to water Biocompatibility: Physical factors and material selection both determine the biocompatibility of a mesh, and biocompatibility can vary over time in vivo. Biologic meshes may have highly biocompatible materials—as they are simply matrices of native, non-immunogenic materials—but may elicit short-term reactions to processing aids that are used to rid them of antigens. Synthetic meshes may be absorbable or permanent. Absorbable meshes could be viewed as entirely "biocompatible" in the long run because they fully disappear. In the short run, their biocompatibility is determined by immunogenicity of their material, the breakdown products, the time horizon over which they break down, the acidity of the environment created by their breakdown, and other factors. The biocompatibility of permanent meshes is determined by the immunogenicity of their materials, under the assumption that they will not breakdown or change over time. For any of these types of mesh, physical factors play a role in biocompatibility as well. (FIG. 2) Generally speaking, and all else equal, finer (thinner) fibers yield more biocompatible material than thicker fibers, larger pores yield more biocompatible material than smaller pores, and flexibility yields more biocompatible material than rigidity. Material grammage, thickness, and other factors have also been implicated.

Physical Properties: Design and manufacture of a surgical mesh carries many of the same considerations as a traditional textile. Meshes can be made with yarns or fibers of different types, sizes or materials. They can be made by knitting, weaving, spinning, etc. They can be treated thermally or chemically. These considerations alter basic fabric characteristics—such as thickness, handling, compliance, strength, etc.—which are often tested using the same industry standards used by the traditional textile industry. Unlike the traditional textile industry, however, these considerations also affect biocompatibility as discussed above.

Thus, the design and manufacture of a surgical mesh must take into account the complex interplay of the fixed characteristics and sensitivities of various polymers, the limitations of current sterilization techniques, and the need for biocompatibility—all within the constraints of providing a fabric of adequate strength and handling to be useful for the surgical repair of soft tissue defects.

Figure 1:
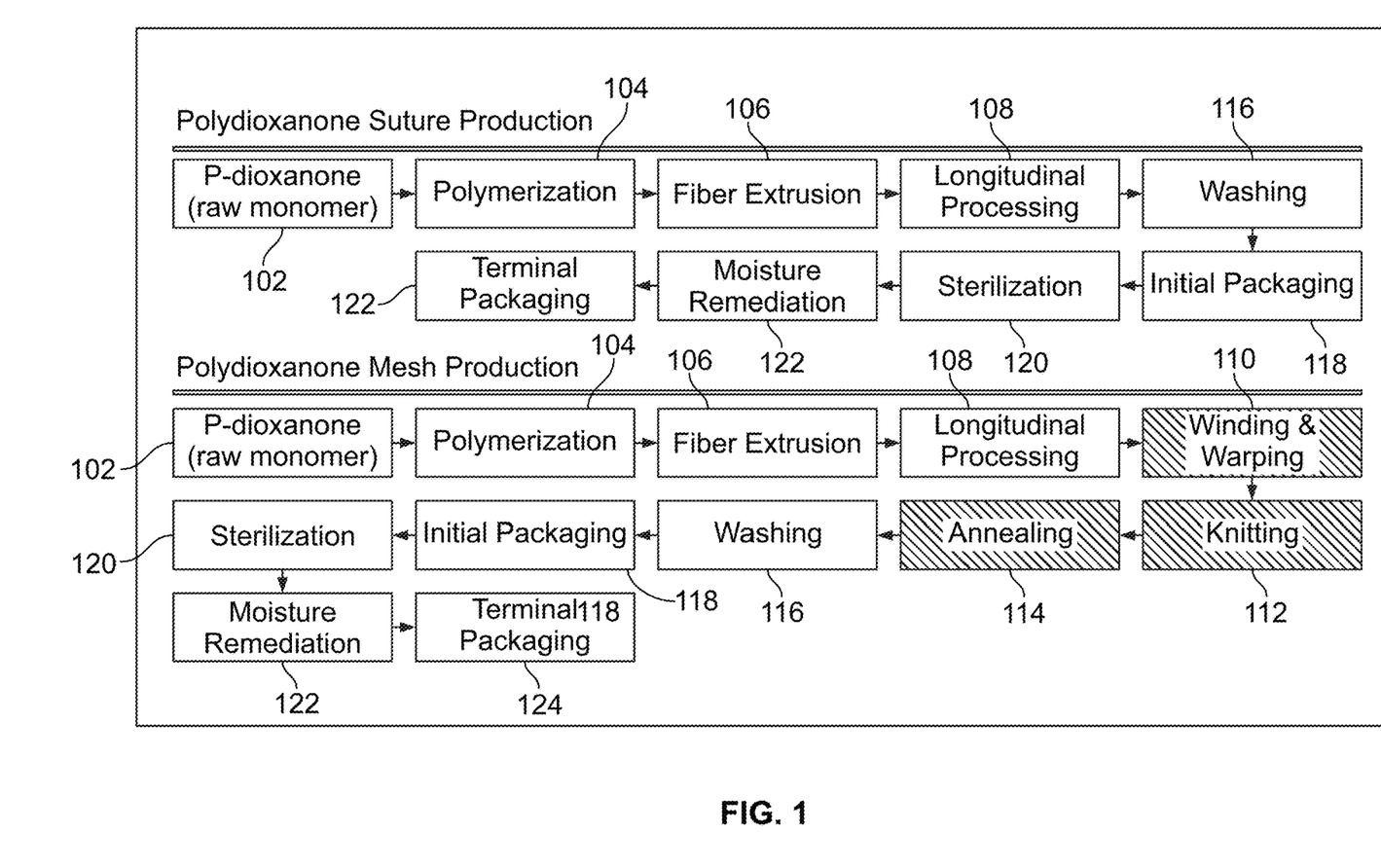
FIG. 1 illustrates stepwise production process for sutures (e.g., Polydioxanone sutures) and mesh (e.g., Polydioxanone mesh), according to an embodiment. Production process steps unique to mesh production are shown in boxes with diagonal repeating lines.

Turning to FIG. 1, a method for creating a surgical mesh according to an embodiment will now be described. It should be noted that some of the steps may also be used to create suture, which is set forth in a parallel set of process blocks in the top half of the diagram.

At process 102, the method involves sourcing raw P-dioxanone monomer. At process 104, P-dioxanone monomer is chemically polymerized (combined) to create poly-p-dioxanone (PDO). The PDO is then forced through a die so that it is discharged as small pellets. At process 106, the PDO pellets are melted and extruded through a mold to create a plurality of individual filaments (PDO fibers). At process 108, the filaments undergo longitudinal processing. That is, the PDO fibers are stretched at a tension of about 0.5 Newtons (N) to about 6.0 N and with or without simultaneous or subsequent application of heat to form the crystalline structure of the fiber into a long chain. The material resulting from process 108 may itself be packaged and sealed for medical use as PDO suture material.

According to an embodiment, at process 110 the PDO fibers are transitioned to a knitting machine where they are wound and loaded into adjacent rows and columns. The PDO fibers are then knitted (process 112) into a mesh whose pores are, for example, of a size that permits circumscription of a circle that may be slightly smaller than 800 microns in diameter (e.g., a quadrilateral whose short axis is slightly less than 800 microns). Once knitted, at process 114, the mesh is annealed by the application of heat under tension, which increases the pores to a size that permits circumscription of a circle that is at least 800 microns in diameter (e.g., a quadrilateral whose short axis is greater than 800 microns). In one implementation, the temperature of the heat applied is 65 degrees Celsius (or approximately 65 degrees Celsius) to 110 degrees Celsius (or approximately 110 degrees Celsius) (i.e., within 40% or within approximately 40% (e.g., up to 45%) of, but not exceeding, the melting point of a material out of which the fiber is constructed—e.g., if the fiber is made of PDO, then within 40% or approximately 40% of the melting point of PDO) for a period of time ranging from 1 hour (or approximately 1 hour) to 9 hours (or approximately 9 hours) at a tension ranging from 4.0 N/cm (or approximately 4.0 N/cm) to 32 N/cm (or approximately 32 N/cm). After heat treatment, in an embodiment, the mesh has a basis weight between and including 30 grams (or approximately 30 grams) per square meter and 140 grams (or approximately 140 grams) per square meter. Furthermore, after process 114, the absorption profile of the mesh is altered. In an embodiment, the heat and tension applied to the surgical mesh is sufficient to modify its absorption profile so that the surgical mesh retains non-zero strength (e.g., more than zero Newtons ball burst strength) for approximately three months after an insertion of the surgical mesh into living tissue, continues to be present in the living tissue from approximately three months after the insertion and approximately six months after insertion, and then disappears relatively soon after six months (before one year after the insertion).

In an embodiment in which the mesh is made from PDO fibers, the heat treatment temperature at process 114 may be far from the melting point of the polymer, such as approximately 65 to approximately 75 degrees Celsius under higher tension and/or for a longer duration (within the aforesaid ranges), which may preferentially alter the absorption profile in order to extend it beyond what is expected from the fiber itself. In another embodiment, the heat treatment temperature may be closer to the melting point, such as approximately 75 to approximately 85 degrees Celsius under lower tension and/or for a shorter duration (within the aforesaid ranges), so as to preferentially alter mechanical properties or dimensional/shape characteristics.

At process 116, the mesh is washed in an ultrasonic bath using a solute such as isopropanol or other volatile agent that can solubilize both polar and non-polar contaminants. At process 118, the mesh undergoes initial packaging, including the application of an inner pouch that functions as a sterile barrier and is permeable to moisture and the application of an outer pouch. In an embodiment, the inner pouch is polyethylene with Tyvek® backing. The outer pouch also functions as a sterile barrier, but is partially permeable to Ethylene Oxide. According to an embodiment, the inner pouch and outer pouch are constructed in a way that allows for later removal of the permeable portion (i.e., the outer pouch) without compromise of the sterile barrier (i.e., the inner pouch). In an embodiment, the outer pouch is a foil pouch that is constructed to be longer than the inner pouch that it contains. In such embodiment, the overage, also called a header, is made of Tyvek®.

At process 120, the mesh is sterilized. In an embodiment, this sterilization process is carried out by exposing the mesh to Ethylene Oxide (ETO) gas in a chamber for a period of time ranging from about 4 hours to about 6 hours at a temperature that ranges from about 115 degrees Fahrenheit to about 125 degrees Fahrenheit. At process 122, the mesh undergoes a moisture remediation process, which, according to an embodiment, involves aerating the mesh in ambient air at a temperature that ranges from about 80 degrees Fahrenheit to about 130 degrees Fahrenheit for a duration of time that does not exceed 12 hours. At process 124, the mesh undergoes a terminal packaging process, which involves removal of the moisture-permeable portion of the outer pouch described in process 118, and approximately simultaneously creating a new seal in order to avoid compromising the sterility of the interior of the pouch. This sterilization process may be used for other products besides surgical mesh. In other words, it can be applied to any product that needs sterilization without the mechanical properties of the product being compromised by hydrolytic degradation during the sterilization process. In an embodiment, this sterilization process is carried out without dwell time. Dwell time is the actual time during which a material to be sterilized is exposed to specific process conditions, which include gas dwell and pre-conditioning dwell. Other cycles with higher heat, higher dwelling time, and higher relative humidity have been tried and demonstrated to have negative effects on performance characteristics of the invention described herein.

In embodiment, the resulting mesh can be three-dimensional through the addition of the appropriate steps. For example, the resulting mesh may take many forms such as an elliptical boat, a hollow hemisphere, or an approximately spherical bag in order to provide a device better suited for breast surgery. Such forms may be made by the heat treatment process disclosed herein, but with the tension applied over a curved surface such as a spherical or elliptical mandrel.

Figure 2:
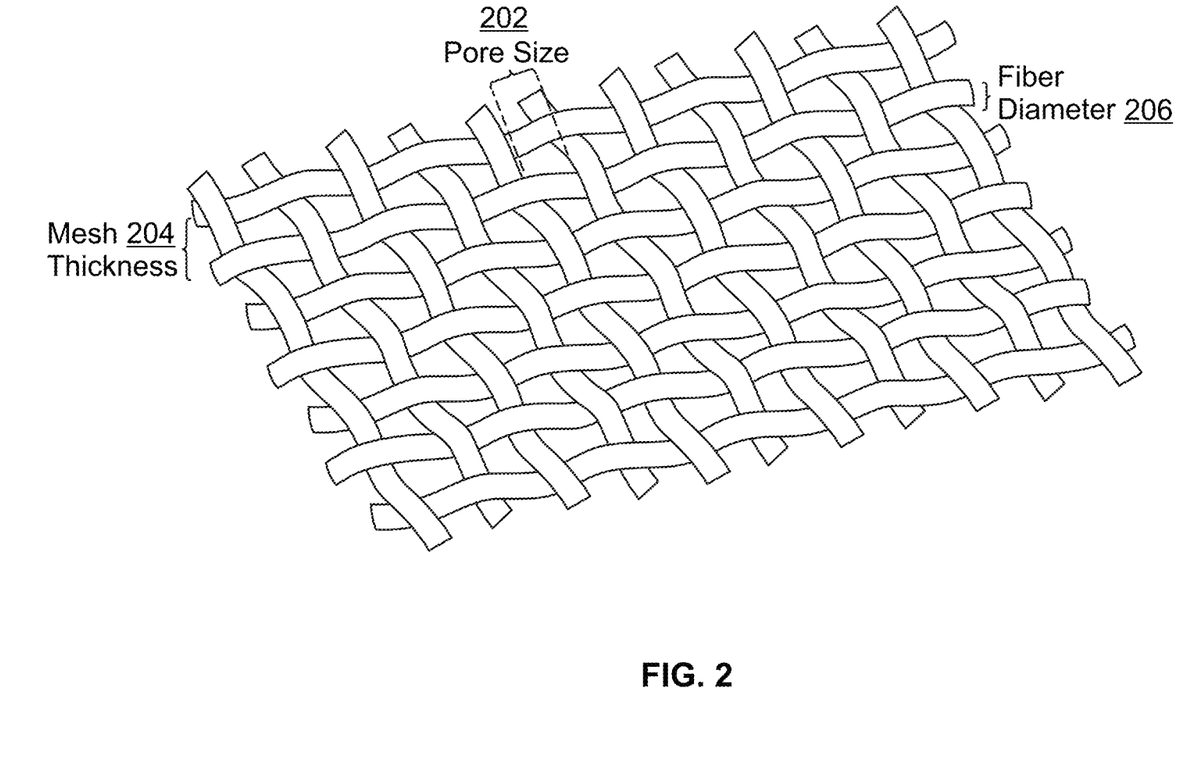
FIG. 2 is a close-up of a reference surgical mesh with "fiber diameter," "thickness," and "pore size" all indicated and "weave pattern" generally visible.

Turning to FIG. 2, an example of how a mesh resulting from the manufacturing process of FIG. 1 is configured, according to an embodiment. In this example, the pore size 202 exceeds 800 microns (micrometers), the thickness 204 is between approximately 0.5 mm and 1 mm, and the diameter 206 of each fiber is between approximately 100 microns and 150 microns.

The process set forth herein confers certain desired characteristics to the end product (the surgical mesh) such as a desirable shape, rigidity, and elasticity. Each step in the process exposes the fiber to a range of temperatures and humidity levels that further degrade strength in comparison to the constituent sutures at their baseline.

In an embodiment, the polydioxanone-based mesh undergoes several more stages of secondary processing, sterilization and moisture removal, with transport outside of the initial manufacturing facility, increasing exposure and encouraging the hydrolytic degradation that began at polymerization. Fine-diameter fibers (USP 5-0) are selected for increased biocompatibility as discussed above, but are known to lose strength at a faster rate than larger fibers. Persons of skill in the art would expect that the resulting mesh would provide inadequate strength or lesser strength retention (significantly less than 3 months).

Figure 3:
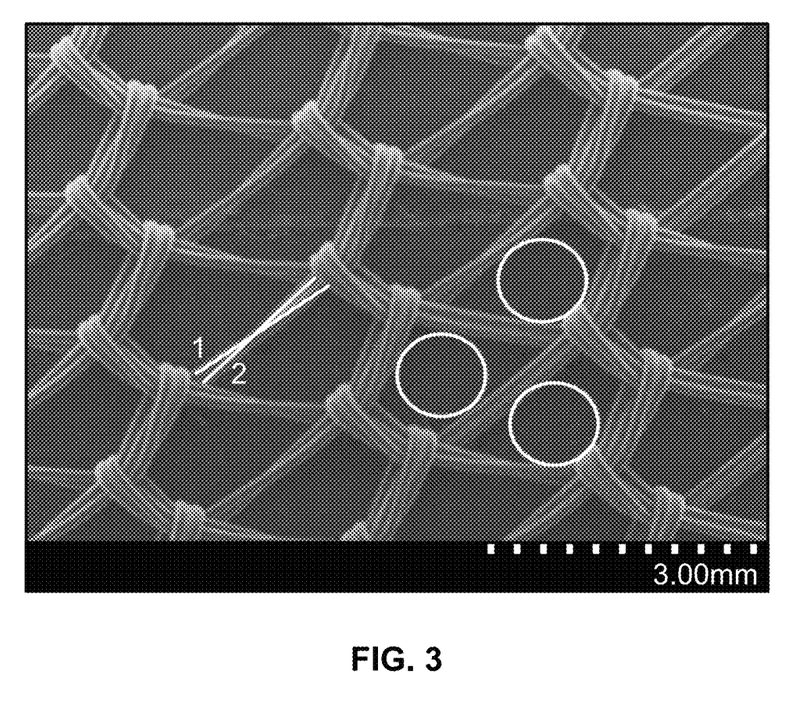
FIG. 3 illustrates an SEM micrograph of polydioxanone mesh in an embodiment showing its knit pattern and sequential formation of interlinking loops in a 'doubled barred' pattern of the monofilament knit, according to an embodiment. The circles show the uniform pore size resulting from the knit pattern. A scale bar is provided in the lower right corner.

According to an embodiment, process 112 of FIG. 1 uses a warp knit, endowing the mesh three dimensionality that allow the fibers to form stable porosity by direct interface/ knitting between adjacent fibers. Further the sequential formation of interlinking loops in a 'doubled barred' pattern (see, e.g., FIG. 3) allows for the compensatory balancing of strength that would otherwise be unavailable to a single suture strand or simple knit pattern. In other words, with hydrolytic degradation occurring stochastically along the length of a given fiber, increased numbers of redundant/ adjacent fibers yields a more uniform and predictable strength loss.

As noted above with respect to process 120 of FIG. 1, in an embodiment, sterilization of the mesh is performed by the use of ethylene oxide gas. The goal is to achieve to achieve a $10^{-6}$ sterility assurance level (SAL), which expresses the probability of a single given finished unit not being sterile. This is a standard requirement for finished medical devices that are labeled as "sterile." Typically achievement of this SAL requires a humid environment, as water is a carrier molecule for Ethylene Oxide. This directly opposes the goal of creating a sterile mesh that has adequate strength and adequate strength retention if the mesh is made of a hydrolytically degradable polymer such as polydioxanone. However, according to an embodiment, the sterilization cycle parameters are tweaked with respect to cycle time, relative humidity, temperature, dwell time, injection rate, etc., to avoid a significant decline in performance characteristics.

In an embodiment, custom sterilization 'parameters', or ranges are established for process 120, within which additives and process steps are maintained in order to balance the need for sterility with the need for a none or less-degraded sterile product. This collection of ranges and specifications constitute a validated sterility cycle, whereby ethylene oxide gas is injected at ~600 Milligrams per liter (Mg/l), chamber temperature is maintained in a (comparatively) low range of 75-95 degrees Fahrenheit, and relative humidity levels in the chamber are maintained below 40%. Each parameter is refined to ensure the maintenance of the desired mechanical characters of the end product, in spite of the added processing and handling that occurs during this step.

In an embodiment, process 122 involves drying the mesh in a vacuum oven through a sterile but water-permeable portion of its packaging. Parameters including time, rate of pull, periodic filtered-air flushes, and temperature are adjusted to avoid water crystallization and to attempt to remove substantially all moisture by evaporation in a time frame that is conducive to routine manufacturing. For example, the process may involve using a hermetically-sealed chamber with a vacuum applied to bring the pressure down to sub-atmospheric levels, injecting filtered air to bring it slightly back up, applying the vacuum to step down the pressure even further, and repeating this cycle until <10 millimeters of Mercury (mmHg) is reached. This process sequentially purges water through evaporation or sublimation, without allowing it to crystallize under a sudden pressure drop and then remain on the product until the end of the process. This helps the mesh maintain stability of its performance over time. If excessive moisture remains, the mesh may degrade by hydrolysis over time in its packaging. After drying, the mesh packaging is sealed to exclude the water-permeable portion.

The most common site of surgical mesh reinforcement is the abdominal wall, where its use has been well-validated to improve the success of inguinal and ventral herniorrhaphy, together accounting for millions of procedures per year. Historically, permanent synthetic meshes predominated, and were over-engineered for strength to prevent mesh failure and hernia recurrence. Several authors have modeled the human abdominal wall and the pressure therein, and found that most commercial mesh products exceed by 100% or more the necessary strength for these repairs. Unfortunately, the focus on strength has not come without human cost, and the estimated rates of chronic pain or foreign body sensation following inguinal hernia repair are in the 10-20% range. In addition, late-presenting infections, erosions/fistulas, and other complications have been reported. The last 30 years have brought a focus on the characteristics of fabrics that alter their biocompatibility, as discussed above. A growing body of literature delineates the physical characteristics that increase biocompatibility, and thus decrease long-term inflammatory reactions and scarring/contracture, and therefore pain and foreign body sensation. During this time, permanent synthetic meshes with fine fibers, light-weight, large pore size, and other favorable physical characteristics have seen increased use.

Figure 4A:
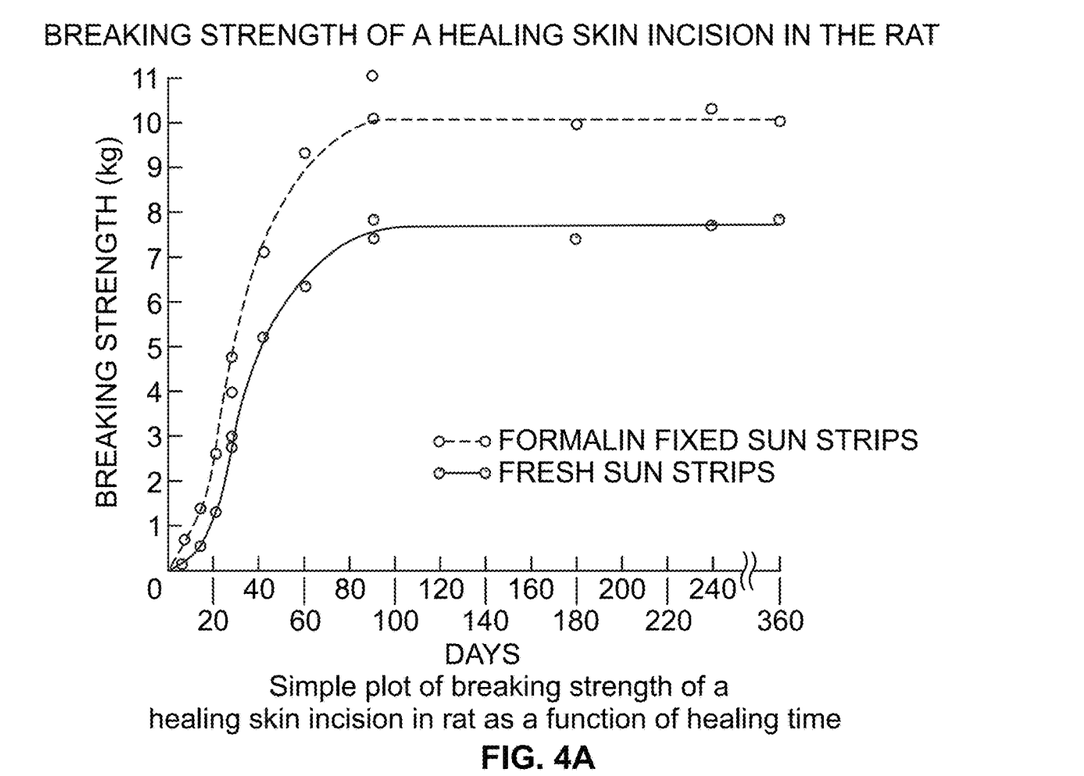
FIG. 4A, FIG. 4B, and FIG. 4C are diagrams and data tables from studies illustrating how embodiments described herein yield unexpected results.
Figure 4B:
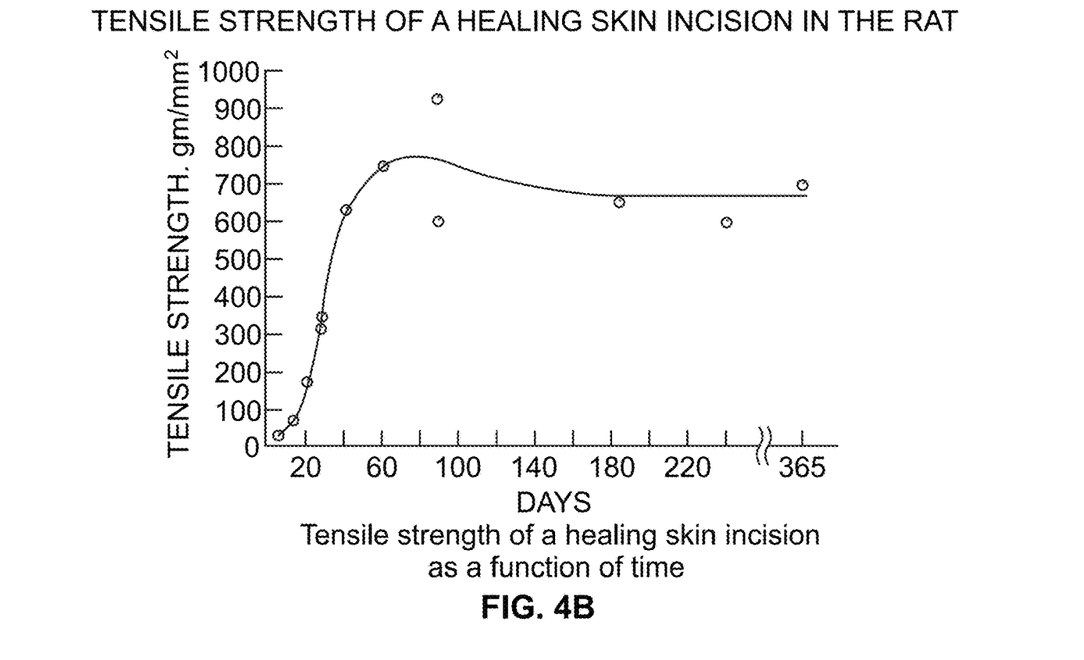
Figure 4C:
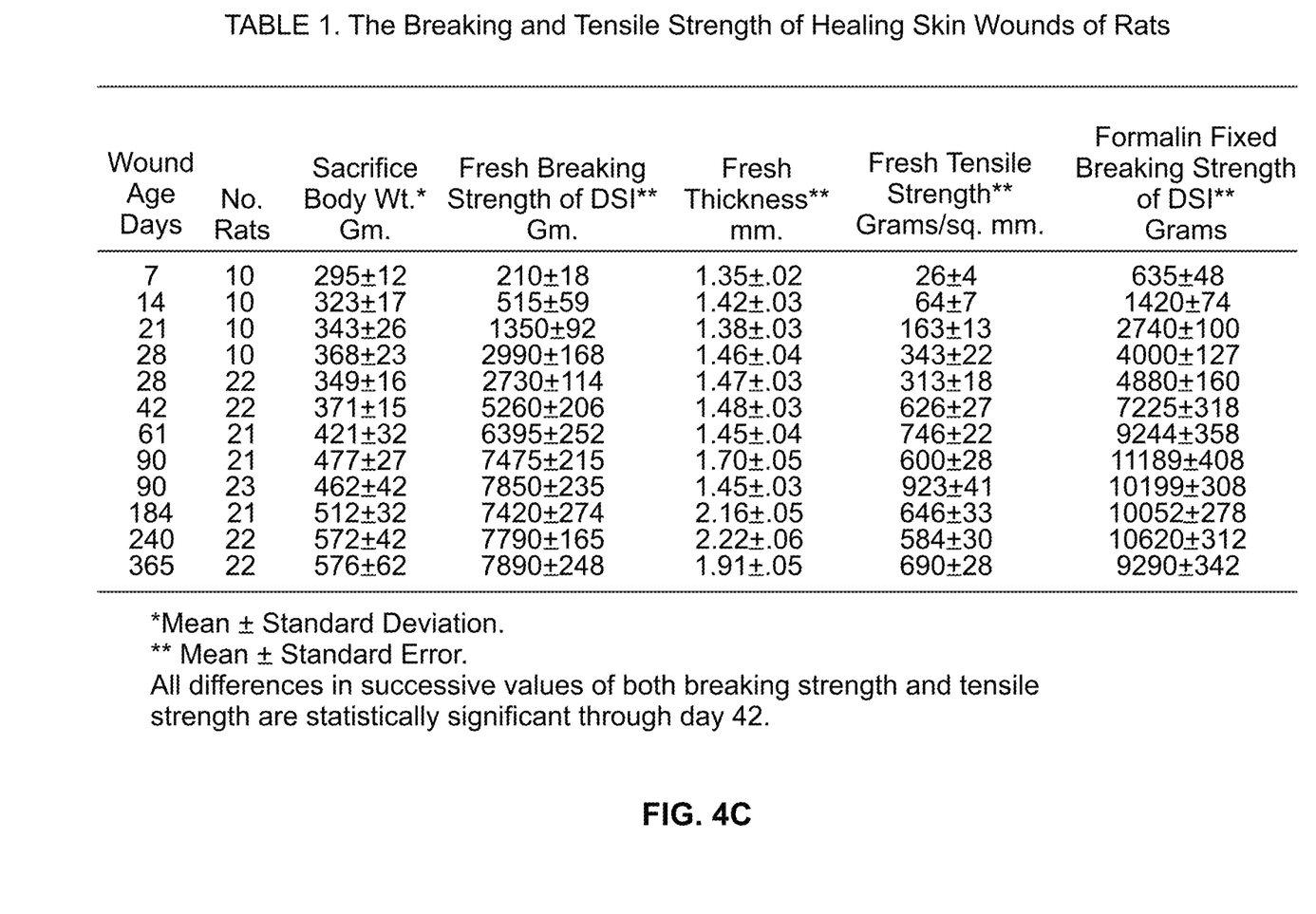

More recently, a central question in the surgical community is whether permanent material is needed in all cases. Fully-absorbable products are entirely biocompatible in the long run, because they are no longer present to cause a reaction. If a mesh can be used to lend strength until the healing surgical wound or defect recovers its own strength, and then disappear thereafter, surgeon and patient could get the best of both worlds. Near-term soft tissue support without long-term complication risk would provide an ideal balance. To ascertain the timeline over which at least some additional strength is desirable, one can turn to classic studies by Levenson et al., which delineate the approximate timing of wound strength recovery. In an animal model of surgical wounds with sequential strength testing over time, strength values reached a plateau at approximately 3 months. Key diagrams and data tables from the studies conducted by Levenson et al. are provided in FIG. 4A, FIG. 4B, and FIG. 4C.

Figure 7:
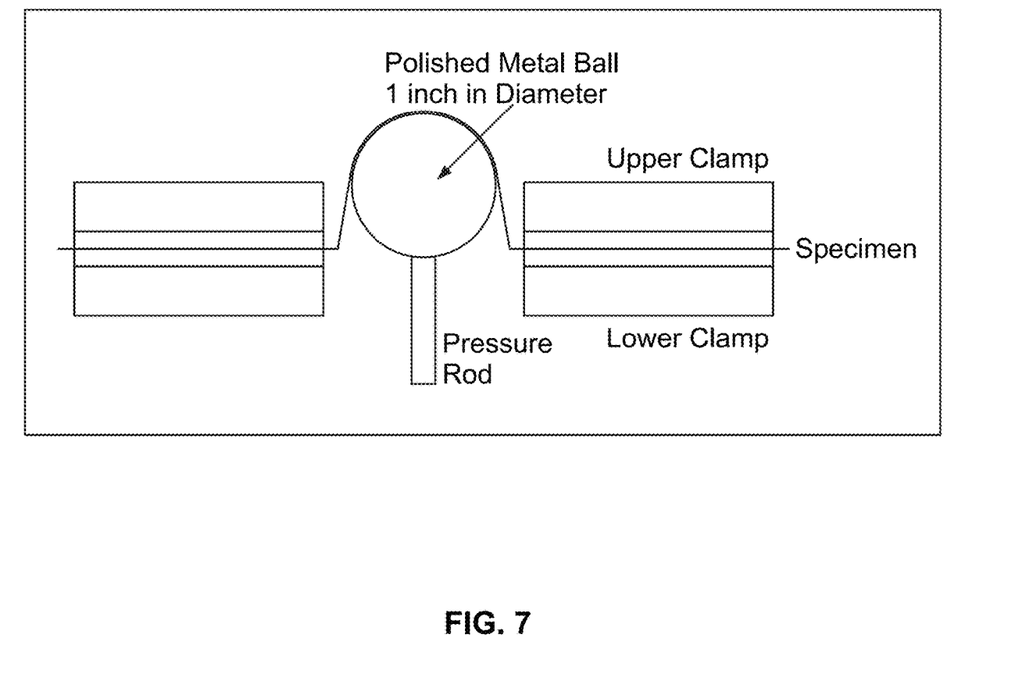
FIG. 7 illustrates a spherical metal probe (ball burst fixture).

Thus, an ideal balance would be achieved in an absorbable surgical mesh that loses its strength over approximately 3 months, transferring the responsibility of load-bearing to the surrounding tissue as that tissue recovers the strength to handle it. The most clinically relevant way of testing strength (used by Levenson, and numerous other researchers) is with a ball burst fixture. This is a spherical metal probe that is forced through mesh, tissue, or other test material that is held clamped circumferentially around a hole through which the probe travels (shown in FIG. 7.) With respect to the ideal timing of full disappearance of a given mesh, its biological relevance once it lacks inherent strength is an important consideration. There is evidence that the foreign body reaction itself, with continued collagen deposition and remodeling, will continue to increase the strength of the wound site for approximately 6 months. It is generally accepted in plastic and general surgical literature on soft tissue repair that 1-year results are generally stable. Beyond one-year, the risk-reward profile of continued foreign body "support" compared to the continued foreign body reaction and attendant risk is questioned. This is supported by the preclinical data discussed herein.

Figure 9:
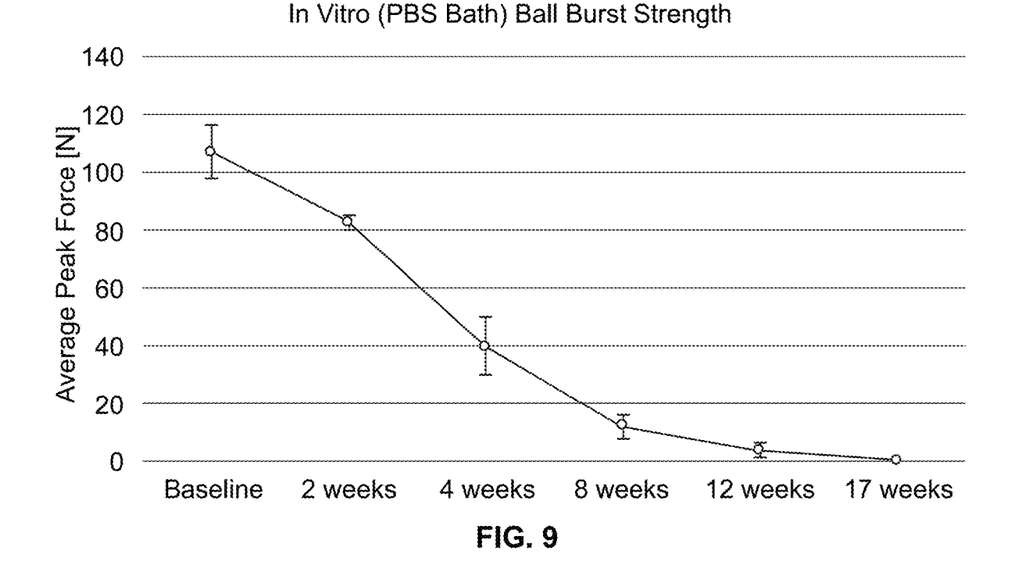
FIG. 9 illustrates a graph showing the results from mechanical ball burst strength testing of an embodiment of the mesh (polydioxanone) after 17 weeks of exposure in a 1× phosphate buffered saline (PBS) bath at approximately 37 degrees Celsius.

According to an embodiment, a surgical mesh configured and produced as described herein starts out with some baseline strength, then over time falls to zero strength over time, and the point at which it falls to zero strength between three and four months after implantation in living tissue (see, e.g., FIG. 9, in which mesh according to an embodiment was tested in a PBS bath).

An advantage of a surgical mesh configured according to an embodiment is that it strikes an ideal balance between strength retention and absorption. Specifically, the surgical mesh retains some strength for at least 3 months, continues to be present between months 3 and 6, and then disappears relatively soon after 6 months (for example, within one year) to minimize long-term adverse events that could result from the continued presence of a foreign body.

Polydioxanone is a biocompatible polymer that was developed in the early 1980's to overcome physical challenges that other bioabsorbable polymers faced with respect to strand flexibility. They are said to have only been surgically useful in the finest of sizes. Contrastingly, polydioxanone can be formed into a flexible strand of a variety of sizes.

Figure 5:
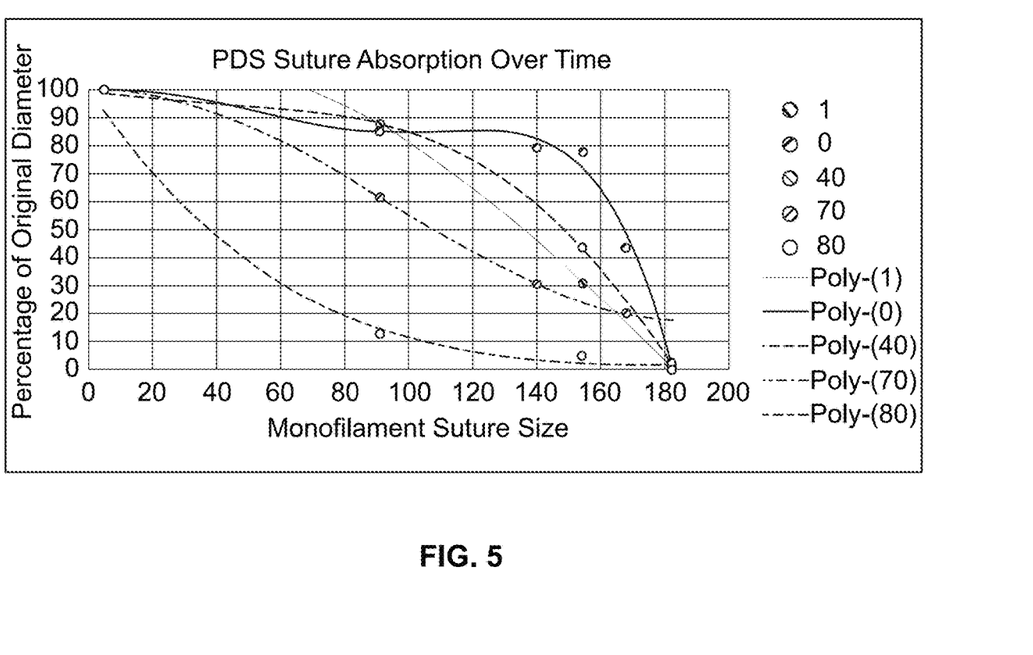
FIG. 5 illustrates PDS suture absorption over time as demonstrated by initial rat studies.
Figure 6:
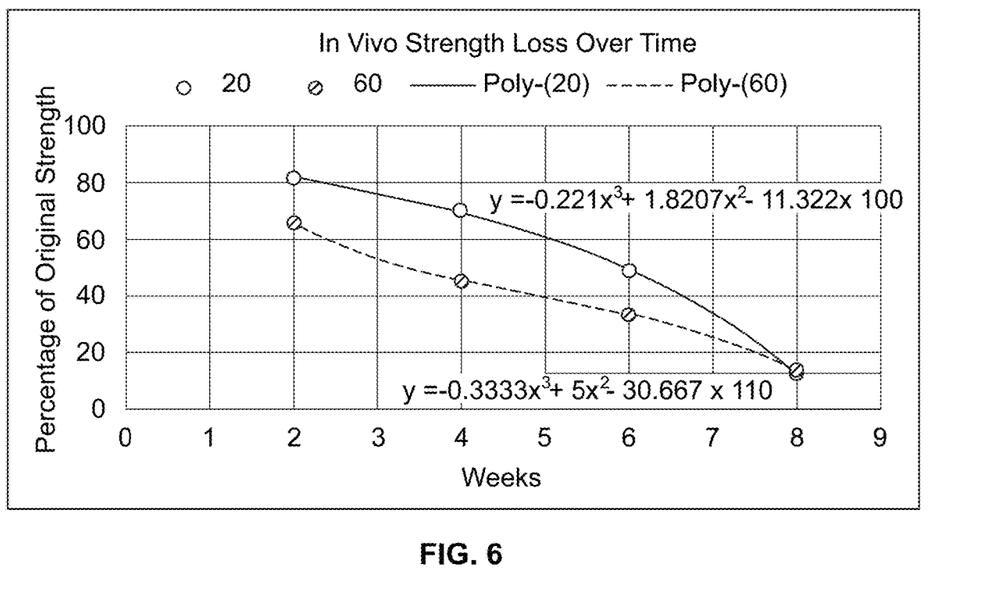
FIG. 6 illustrates in vivo strength loss of PDS sutures over time as demonstrated by initial rat studies.

An initial rat study by the discoverers of Polydioxanone demonstrated polydioxanone's in vivo degradation and strength loss over time. The results from this initial rat study are shown in FIG. 5 and FIG. 6. Results demonstrated that smaller diameter threads absorbed more quickly and also lost strength more quickly. In general, the suture threads were absorbed completely in around 180 days. Another study in rats demonstrated that 5-0 PDO sutures in particular are completely absorbed at exactly 6 months. The time to complete loss of strength was 8.25-8.5 weeks.

Due to the flexibility, strength retention, and degradation profile, it has become one of the most commonly used absorbable suture materials throughout the body.

Various additional embodiments of a surgical mesh will now be described. The surgical mesh has absorption and strength characteristics that are unexpected in light of the current understanding in the art. Design parameters for various embodiments of the surgical mesh of the present disclosure include a double-bar, warp knit pattern, 5-0 USP fiber diameter, and monofilament fibers comprised of a polydioxanone thermoplastic polymer. Results from in vitro and in vivo testing are included that show strength retention of the mesh after 4 months and full absorption of the mesh after 6-9 months.

A description of how an embodiment of the surgical mesh is manufactured will now be described. First, it should be noted that medical devices such as absorbable PDO mesh and suture that are subject to degradation via hydrolysis exhibit reduced mechanical strength from the moment the device is manufactured through full absorption in the implanted specimen. Moisture level and degradation are characterized and tracked throughout the manufacturing process and measured via validated test methods such as Molecular Weight (units Dolton) Analysis (determining the average and range of lengths sizes of the polymer chains in the material) and Inherent Viscosity (units dL/g, a reflection of molecular weight of the mesh sample). The degradation mechanism of Polydioxanone is hydrolysis, meaning that water or moisture will promote the degradation. Typically, hot and/or high humid or water conditions and increased exposure time, including processing steps/storage will lead to quicker degradation and therefore impact the polymer stability (as measured by molecular weight or inherent viscosity) and strength retention. To describe the molecular weight distribution of a polymer numerically, three different molecular weight averages are commonly used. These are the number average molecular weight (Mn), the weight average molecular weight (Mw), and the Z average molecular weight (Mz). Mn provides information about the lowest molecular weight portion of the sample. Mw is the average closest to the center of the curve and Mz represents the highest molecular weight portion of the sample. For the purposes of raw material input measurements for the polymers described herein, Mw provides the most useful metric, as utilized in FIG. 8 and FIG. 11. In an embodiment, the completed mesh is approximately 80 kiloDaltons (kDa) to approximately 200 kDa, the Mn is between approximately 55 kDa and 75 kDa, and the Mz is generally between 200 kDa and 450 kDa.

Figure 8:
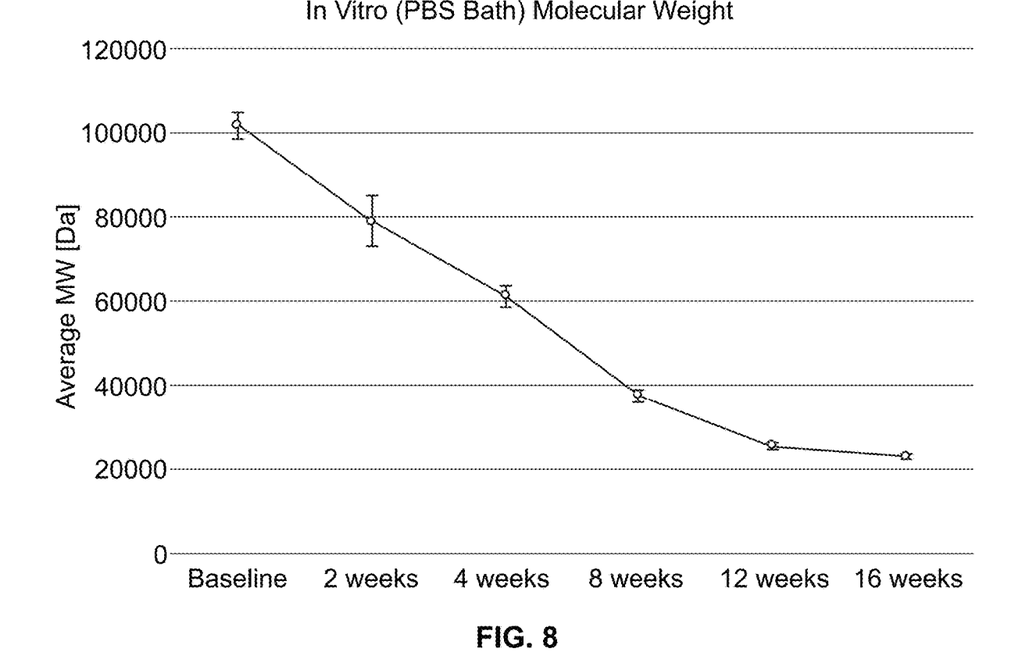
FIG. 8 illustrates a graph showing the results from molecular weight testing of an embodiment of the mesh (polydioxanone) after 17 weeks of exposure in a 1× phosphate buffered saline (PBS) bath at approximately 37 degrees Celsius.

The polymer fibers of the mesh are known to degrade during knitting, stretching/heating, packaging and sterilization processes, which led to the original expectation that the final mesh would have equal or less strength and a shorter degradation timeline than a single fiber that has not undergone this processing. This was the expected result. However, this is not what was observed from in vitro testing. FIG. 8 Shows the data collected regarding molecular weight (MW) of an embodiment of the surgical mesh after 17 weeks of exposure in a 1× phosphate buffered saline (PBS) bath. This data shows that after 17 weeks, the mesh had yet to fully degrade and would likely last 6 to 9 months before fully absorbing. This finding is bolstered by results from mechanical ball burst testing conducted on samples from the PBS bath. FIG. 9 shows that the mesh retains some burst strength for at least 4 months.

Figure 10:
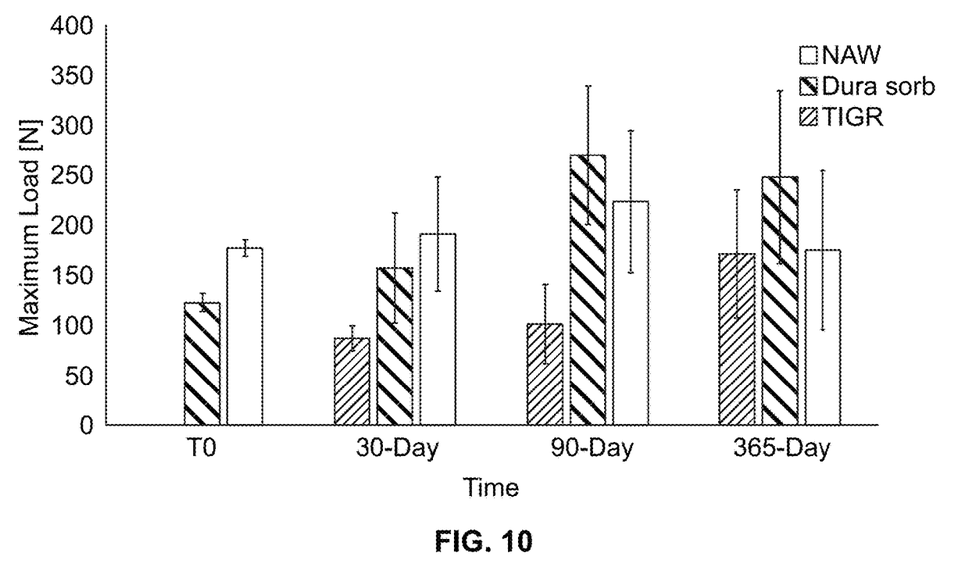
FIG. 10 illustrates a graph showing results from in vivo mechanical ball burst testing of an embodiment of the mesh.
Figure 11:
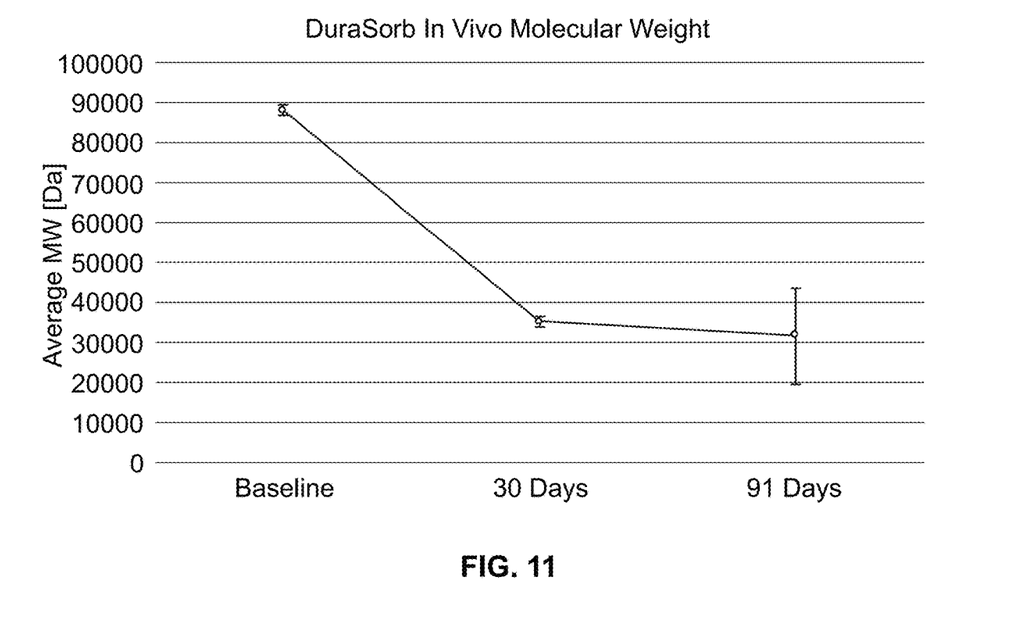
FIG. 11 illustrates a graph showing results from in vivo molecular weight testing of an embodiment of the mesh.

In vivo investigations of an embodiment of the surgical mesh confirmed the in vitro absorption timeline results. In a 6-month intramuscular implantation study in a rabbit model, 33% of sample sites showed remaining implant material left when analyzed under light microcopy. These results are also mirrored with in vivo testing conducted in a large animal model (porcine). Molecular weight and ball burst analysis were conducted in a porcine model. FIG. 10 shows results from ball burst testing which show the repair site gaining strength over time and continually showing a higher burst strength than the native abdominal wall tissue. Native abdominal wall tissue from the study model were also tested at both 30— and 91— day time points. FIG. 11 shows the molecular weight of the mesh decreasing over time, but not showing full degradation after 91 days.

An embodiment of the mesh was engineered with specific process considerations that appear to have decreased the degradation rate by hydrolysis after implantation. These parameters include but are not limited to: PDO of average molecular weight greater than 85 kDa (as measured by the methods described herein), fiber diameter of USP 5-0, double bar warp knit pattern, thickness less than 1 mm, and low-temperature, low-humidity sterilization method, heat treatment and post-sterilization vacuum drying cycle with successive purges by filtered air, neutral gas, or other anhydrous environment. By manipulating these factors, a mesh was created that fully realizes the biocompatibility of PDO while utilizing a fiber of low diameter. The combination of these factors, especially the heat treatment conditions have led to a mesh with an unexpected bio absorption and strength retention profile lasting beyond the six-month time horizon typical for this material in 5-0 USP sized monofilament form.

This disclosure revealed a method to improve the performance of a biodegradable surgical mesh after implantation and the application of such biodegradable surgical mesh during breast reconstruction procedures. More specifically, the revealed method is a heat treatment method to improve the mechanical properties of the polymeric fiber after the fibers are knitted into surgical mesh. Such changes in the biomechanical properties of the surgical mesh make the mesh or mesh products have slower degradation rate, less inflammation, and improved host tissue integration, as compared to the suture itself. More specifically, the controlled processing conditions are designed to increase the degrees of crystallization and alignment of the polymeric molecules of the mesh fibers. Furthermore, the controlled process can control the ratio of crystallization and degree of alignment of the polymeric molecules in the mesh and mesh products.

As detailed above, polymeric fibers are typically extruded through an extruding machine under melting conditions. The temperature during extrusion is typically higher than the melting temperature of the polymers. The melted polymers are then forced through a hole or a die and then cooled in water to form the fibers. Polymeric molecules are typically partially crystalized in the fiber due to the rapid cooling process which does not give the polymer molecules sufficient amount of time to nicely organize themselves. After knitted into mesh, the fiber properties are then carried through into the mesh. The current art uses an annealing or heating process to flat the mesh or to form a predetermined 3-dimensionally stable structures. In this disclosure, we revealed that when the knitted mesh is placed under certain specific 2-dimensional tension at a certain temperature closer to the polymer's melting point for a given period of time, the resulting mesh will demonstrate significantly different properties after implanted in vivo, such as different degradation rate or slower degradation or longer in vivo life, as well lower inflammation as compared to fibers before made into mesh. This property could benefit certain clinical applications, such as reconstructive abdominal surgery, reconstructive breast surgery, and other forms of general and plastic surgery requiring soft tissue support.

Figure 12:
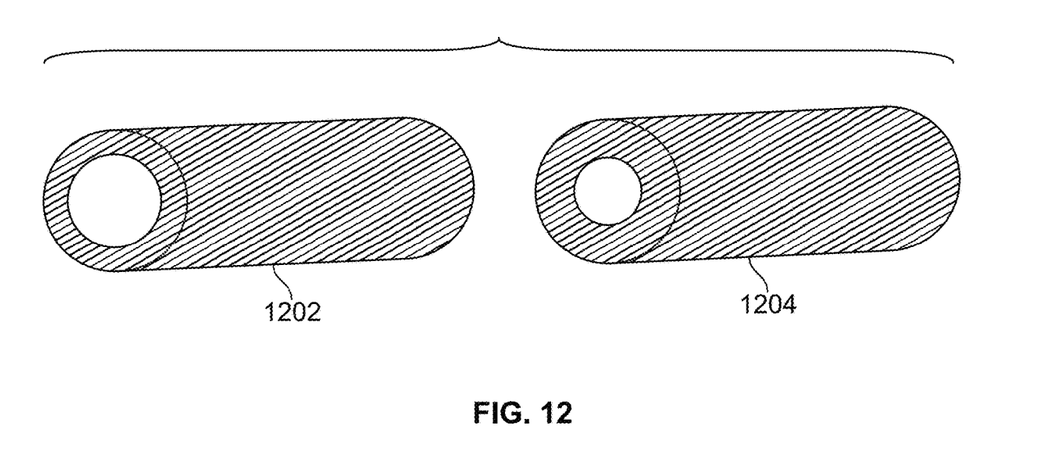
FIG. 12 is an oblique view of the cut ends of two fibers according to an embodiment.

Heat treatment at close to the polymer's melting temperature under tension improves the movability of polymer molecules with minimal or even no noticeable dimensional change to the fiber size. The resulted degree of changes of the mesh product depends upon the combination of selected range of temperature, tension applied, and duration of the treatment. Furthermore, such heat treatment is generally lead to improved fiber surface smoothness, which decreased the fiber surface area exposed and in turn decreased the hydrolysis speed. Higher degree treatment often leads to fibers with a thicker layer of highly recrystallized polymer molecules, and therefore a slower degradation rate in vivo, as illustrated in FIG. 12 (reference numeral 1202 illustrating an oblique view of a fiber with light treatment and low depth of penetration, while reference numeral 1204 illustrating a fiber treated with higher temperature, higher tension, or longer duration).

The higher the treatment temperature, the longer treatment duration, and higher tension during such heat treatment will lead to stronger mesh product, slower in vivo degradation, improved tissue integration, and less inflammation. This property is typically required for surgical mesh during reconstruction surgeries, as less, but stronger material could be used to achieve better clinical outcome.

Various embodiments described herein may use a dioxanone-based polymer having a melting point of approximately 105 to 115 degrees Celsius. The treatment temperature for these polymers may be in the range of approximately 65 to approximately 110 degrees Celsius, depending upon the treatment durations.

The biomechanical benefits supporting the use of a partially load-bearing construct over a permanent fully load-bearing one has been established in the orthopedic and orthognathic literature. Two main techniques for bone reparation are: (1) rigid fixation, in which the hardware or implant used prevents micromotion and provides the vast majority of load bearing, and (2) semi-rigid or load-sharing fixation, in which the implanted construct merely supports the bone, which assumes most of the functional load. Basic science investigations have demonstrated that, as compared to rigid fixation, semi-rigid fixation improves the stability, strength, and growth capability of the healing bone due to forces being applied on it, stimulating its reparative and trophic potentials, allowing it to regain load -bearing capabilities. Groups have demonstrated the superiority of semi-rigid fixation to rigid fixation in condylar fracture repair, lumbar spine repair, and several other procedures.

There are data demonstrating that pore sizes that allow circumscription of a circle of approximately 800 microns or greater result in more robust soft tissue ingrowth and avoid "scar plating," a phenomenon in which the granulomatous reactions surrounding each strut as it degrades can create a confluent mass that blocks neovascularization, intrapore collagen deposition, and immunologic surveillance. Thus, a mesh with a pore size and geometry that avoids this is desirable. There is also evidence that thinner fibers result in a lower degree of inflammatory foreign body reaction and greater biocompatibility. However, both larger pores and thinner fibers may sacrifice short-term strength and strength retention for long-term strength of soft tissue ingrowth. Thus, after testing numerous design iterations, approximately 100-150 microns in fiber diameter was found to be the smallest fiber that would yield a mesh with acceptable strength. Monofilament fiber was used due to the smaller surface area per unit length, a property which both reduces the rate of surface erosion and reduces potential for bacterial adhesion. Basis weight, or areal density, may be specified as a process control, as it is effected by polymer composition (effects absolute density of base material), fiber size (effects linear density), and pore size (indicates voids in material). Importantly this also effects handling, which is important in the marketing of a surgical device.

Further, the heat treatment under tension described above for the suture is also performed for the mesh, as depicted in FIG. 1. This step is used in this case to contribute to the delayed degradation or the unexpected result described above with respect to mesh strength and degradation through the increase of the degree of recrystallization and/or polymeric molecules alignment in the direction of the fibers. The recrystallization and alignment along the fiber direction for the polymer at the molecular level in the mesh fibers that is conferred by this additional heat treatment also effect the strength retention and absorption profile by decreasing the rate of bulk hydrolysis, allowing the treated polymer mesh to exhibit increased longevity as compared the untreated suture/fiber. Further, heat treatment at a temperature close to the melting point of an absorbable polymer decreases the surface roughness of the mesh fibers, therefore decreasing surface interactions with water molecules after implantation and slowing the process of surface hydrolysis, while bulk hydrolysis may be occurring throughout. Between these two effects—one related to surface erosion and one related to bulk erosion—heat treatment parameters can be changed with respect to time and temperature to modify the absorption profile of a mesh made of sutures to exceed the expectations of the sutures themselves. For example, high tension and relatively low heat for a long time will have a greater effect on chain linearity and bulk erosion, while treatment of low tension and high heat for a short time will have a greater effect on the surface characteristics and surface erosion of the mesh fibers.

Custom, finely calibrated ethylene oxide sterilization 'parameters' or ranges were titrated to confer the desired end-state mechanical performance on a finished absorbable mesh device. These parameters allow manufacturers to avoid the significant risks to performance that accompany the introduction of high relative humidity (RH) and temperature (degrees F.) consistent with typical achievement of 106 sterility assurance levels (SAL) via ethylene oxide sterilization.

These custom parameters have been successfully validated via ISO 11135:2014 Sterilization of health care products—Ethylene oxide—Requirements for development, validation and routine control of a sterilization process for medical devices. The customization effort included the following three activities:

a) Complete elimination of otherwise routine process steps that would subject an absorbable mesh to elevated levels of moisture and heat. In an embodiment, this includes eliminating environmental preconditioning. Environmental preconditioning typically involves exposure to nominal 118 degrees F. and greater than 65 percent relative humidity for a range of 12 to 72 hours.

b) Customization, monitoring and control of processes that cannot be eliminated as they are required to achieve required sterility assurance levels: Absorbable mesh exposure to EtO gas for approximately 5 hours and no more than five hours and five minutes, utilizing a tightly controlled temperature range that does not fall below 115 degrees F. or exceed 125 degrees F.

c) Customization of the ETO outgassing through a controlled Aeration process whereby temperatures range from as low as 80 degrees F., do not exceed 130 degrees F. and routinely remain at approximately 110 degrees F., for a time not to exceed 12 hours, the minimum allowed to ensure operator safety.

This unique combination of sterilization cycle parameters, which are both controlled and closely monitored using temperature and humidity sensors, support the replicable achievement of total inactivation of microorganisms and the achievement of a $10^{-6}$ sterility assurance level.

It should be understood that the embodiments described herein should be considered in a descriptive sense only and not for purposes of limitation. Descriptions of features or aspects within each embodiment should typically be considered as available for other similar features or aspects in other embodiments. It will be understood by those of ordinary skill in the art that various changes in form and details may be made therein without departing from their spirit and scope.

What is claimed is:

1. A method for creating a surgical mesh, the method comprising:
    (a) heat treating a plurality of fibers;
    (b) knitting the plurality of fibers into a mesh; and
    (c) heat treating the mesh by applying heat at a temperature within 40% of but does not exceed a melting point of a material out of which the plurality of fibers are made, while subjecting the mesh to a tension that falls in a range of 4.0 Newtons per centimeter (N/cm) to 32.0 N/cm for a period of time that falls in a range of 1 hour to 9 hours.

2. The method of claim 1, further comprising: while heat treating the plurality of fibers, subjecting each of the plurality of fibers to a tension that falls within a range of 0.5 Newtons and 6.0 Newtons.

3. The method of claim 1, wherein the material is poly-p-dioxanone (PDO).

4. The method of claim 3, wherein the temperature falls within a range of 65 degrees Celsius to 75 degrees Celsius.

5. The method of claim 3, wherein the temperature falls within a range of 75 degrees Celsius to 85 degrees Celsius.

6. The method of claim 1, wherein heat treating the mesh comprises applying heat to the mesh at a temperature that is within a range of 65 degrees Celsius to 110 degrees Celsius.

7. The method of claim 1, wherein the mesh has a plurality of pores, each of which is large enough to circumscribe a circle that is at least 800 micrometers in diameter.

8. The method of claim 1, wherein the mesh after heat treatment has a basis weight that falls within a range of 30 grams per square meter to 140 grams per square meter.

9. The method of claim 1, wherein the mesh is subjected to the tension over a curved surface to shape the mesh into a three-dimensional form.

10. The method of claim 1, further comprising, after step (c):
    placing the mesh in an ethylene oxide chamber without an environmental preconditioning step;
    exposing the mesh to ethylene oxide within the chamber for between and including 4 hours and 6 hours at a temperature between and including 115 degrees Fahrenheit and 125 degrees Fahrenheit without steam injection; and
    without the introduction of additional humidity, aerating the mesh in ambient air for no more than 12 hours at a temperature between and including 80 degrees Fahrenheit and 130 degrees Fahrenheit.

11. The method of claim 1, further comprising, after step (c), a further step:
    (d) applying heat and tension to the surgical mesh sufficient to modify its absorption profile so that the surgical mesh retains non-zero strength for three months after an insertion of the surgical mesh into living tissue, continues to be present in the living tissue from three months after the insertion to six months after insertion, and then disappears before one year after the insertion.

12. A surgical mesh created by a process comprising:
    heat treating a plurality of fibers;
    knitting the plurality of fibers into a mesh; and
    heat treating the mesh by applying heat at a temperature within 40% of but does not exceed a melting point of a material out of which the plurality of fibers are made, while subjecting the mesh to a tension that falls in a range of 4.0 Newtons per centimeter (N/cm) to 32.0 N/cm for a period of time that falls in a range of 1 hour to 9 hours.

13. The surgical mesh of claim 12, further comprising:
    while heat treating the plurality of fibers, subjecting each of the plurality of fibers to a tension that falls within a range of 0.5 Newtons and 6.0 Newtons.

14. The surgical mesh of claim 12, wherein the material is poly-p -dioxanone (PDO).

15. The surgical mesh of claim 14, wherein the temperature falls within a range of 65 degrees Celsius to 75 degrees Celsius.

16. The surgical mesh of claim 14, wherein the temperature falls within a range of 75 degrees Celsius to 85 degrees Celsius.

17. The surgical mesh of claim 12, wherein heat treating the mesh comprises applying heat to the mesh at a temperature that is within a range of 65 degrees Celsius to 110 degrees Celsius.

18. The surgical mesh of claim 12, wherein the mesh has a plurality of pores, each of which is large enough to circumscribe a circle that is at least 800 micrometers in diameter.

19. The surgical mesh of claim 12, wherein the mesh after heat treatment has a basis weight that falls within a range of 30 grams per square meter to 140 grams per square meter.

20. The surgical mesh of claim 12, wherein the mesh is subjected to the tension over a curved surface to shape the mesh into a three-dimensional form.

\* \* \* \* \*